United States Patent [19]

Lardy et al.

[11] Patent Number: 5,506,223
[45] Date of Patent: Apr. 9, 1996

[54] Δ5-ANDROSTENES USEFUL FOR PROMOTING WEIGHT MAINTENANCE OR WEIGHT LOSS AND TREATMENT PROCESS

[75] Inventors: Henry A. Lardy; Ieva L. Reich, both of Madison, Wis.; Yong Wei, Washington Boro, N.J.

[73] Assignee: Humanetics Corporation, St. Louis Park, Minn.

[21] Appl. No.: 327,646

[22] Filed: Oct. 24, 1994

Related U.S. Application Data

[60] Division of Ser. No. 123,151, Sep. 2, 1993, abandoned, which is a continuation-in-part of Ser. No. 867,288, Apr. 10, 1992, Pat. No. 5,296,481, which is a continuation of Ser. No. 575,156, Aug. 29, 1990, abandoned.

[51] Int. Cl.$^6$ .................................................. A61K 31/56
[52] U.S. Cl. .......................................... 514/178; 514/182
[58] Field of Search ...................................... 514/178, 181

[56] References Cited

U.S. PATENT DOCUMENTS 4,898,694  2/1990  Schwartz et al. .................... 260/397.5

OTHER PUBLICATIONS

Phosphates in Foods, Ricardo A. Molins, Ph.D., CRC Press, p. 190 (1982).

Primary Examiner—Theodore J. Criares
Attorney, Agent, or Firm—Faegre & Benson

[57] ABSTRACT

A method for promoting weight control by treating a subject with a therapeutic amount of one of the Δ5-androstenes listed below to stimulate weight control without affecting appetite or inducing the synthesis of sex hormones.

Δ5-Androstenes providing the desired biological activities include:

Δ5-Androstene-3β,7α-diol-17-one (1)
Δ5-Androstene-3β-ol-7,17-dione (2)
Δ5-Androstene-3β,7α,17β-triol (3)
Δ5-Androstene-3β,17β-diol-7-one (4)
Δ5-Androstene-3β-acetoxy-7,16,17-trione (5)
Δ5-Androstene-3β,16α-dihydroxy-7,17-dione (6)
Δ5-Androstene-3β-propionoxy-16β-acetoxy-7,17-dione (7)
Δ5-Androstene-3β,7α,17β-triol-16-one (8)
Δ5-Androstene-3β,17β-diol-7,16-dione (9)
Δ5-Androstene-3β,16α,17β-triol-7-one (10)

and derivatives thereof wherein one or more of the hydroxyl or keto substituents is a group convertible thereto by hydrolysis.

12 Claims, No Drawings

Δ 5-ANDROSTENES USEFUL FOR PROMOTING WEIGHT MAINTENANCE OR WEIGHT LOSS AND TREATMENT PROCESS

This application is a division of U.S. patent application Ser. No. 123,151 filed 02 Sep. 1993 now abandoned, which is a continuation-in-part of U.S. patent application Ser. No. 867,288 filed 10 Apr. 1992, now U.S. Pat. No. 5,296,481, which is a continuation of U.S. patent application Ser. No. 575,156 filed 29 Aug. 1990, now abandoned.

FIELD OF THE INVENTION

The invention relates to the use of steroids for effecting a desired biological response. Specifically, the invention relates to a treatment program using Δ5-androstenes for promoting weight maintenance and/or weight loss (hereinafter referenced collectively as "weight control").

BACKGROUND

The steroid dehydroepiandrosterone (DHEA) is believed to stimulate various biological responses including (i) inducing the synthesis of various thermogenic enzymes which are effective for regulating metabolism and thereby promoting weight control without affecting caloric intake, and (ii) inducing an increase in the production of the sex hormones androgen and estrogen.

The ability of DHEA to promote weight control is believed to be mediated through enhanced thermogenesis (conversion of foodstuffs to heat energy rather than chemical energy such as ATP and/or triacylglycerides). The thermogenic effect mediated by DHEA is believed to result from the ability of DHEA to stimulate the synthesis of thermogenic enzymes including mitochondrial glycerol 3-phosphate dehydrogenase (G3P-DH) and cytosolic malic enzyme (ME). Such enzymes tend to reduce the efficiency of energy metabolism within the body.

Unfortunately, DHEA is generally considered to be ineffective as a weight controlling therapeutic agent because the dosage necessary to achieve weight control frequently produces significant adverse side-effects including substantial increases in the concentration of sex hormones.

Accordingly, a therapeutic agent possessing the weight control characteristic of DHEA without the adverse side-effect of stimulating the synthesis of sex hormones would be extremely useful. In addition, the effectiveness of such a therapeutic agent could be significantly enhanced if the agent possessed an increased weight control activity relative to DHEA.

SUMMARY OF THE INVENTION

A method for promoting weight maintenance and/or weight loss (hereinafter referenced collectively as "weight control") which includes the step of treating a subject with an effective weight controlling amount of a Δ5-androstene which is effective for stimulating the desired biological response of promoting weight control while being substantially ineffective for inducing the undesired biological response of synthesising sex hormones.

Δ5-androstenes providing the desired beneficial biological response without the undesired biological response include:
Δ5-Androstene-3β,7α-diol-17-one (1)
Δ5-Androstene-3β-ol-7,17-dione (2)
Δ5-Androstene-3β,7α,17β-triol (3)
Δ5-Androstene-3β,17β-diol-7-one (4)
Δ5-Androstene-3β-acetoxy-7,16,17-trione (5)
Δ5-Androstene-3β,16α-dihydroxy-7,17-dione (6)
Δ5-Androstene-3β-propionoxy-16β-acetoxy-7,17-dione (7)
Δ5-Androstene-3β,7α,17β-triol-16-one (8)
Δ5-Androstene-3β,17β-diol-7,16-dione (9)
Δ5-Androstene-3β,16α,17β-triol,7-one (10)

and derivatives thereof wherein one or more of the hydroxyl or keto substituents is a group convertible thereto by hydrolysis.

Examples of such hydrolyzable groups include hydroxyl groups esterified with an acid selected from the group consisting of (i) normal or branched, saturated or unsaturated $C_{2-22}$ aliphatic acids, (ii) $C_{7-12}$ aromatic acids, (iii) $C_3$ or larger dicarboxylic acids in which only one of the carboxyl groups is esterified to the hydroxyl group(s) on the steroid, or (iv) inorganic acids such as sulfuric and phosphoric.

DETAILED DESCRIPTION OF THE INVENTION INCLUDING A BEST MODE

The Δ5-androstenes identified below possess a unique combination of properties including the ability to promote weight control without affecting appetite and without stimulating the production of sex hormones.
Δ5-Androstene-3β,7α-diol-17-one (1)
Δ5-Androstene-3β-ol-7,17-dione (2)
Δ5-Androstene-3β,7α,17β-triol (3)
Δ5-Androstene-3β,17β-diol-7-one (4)
Δ5-Androstene-3β-acetoxy-7,16,17-trione (5)
Δ5-Androstene-3β,16α-dihydroxy-7,17-dione (6)
Δ5-Androstene-3β-propionoxy-16β-acetoxy-7,17-dione (7)
Δ5-Androstene-3β,7α,17β-triol-16-one (8)
Δ5-Androstene-3β,17β-diol-7,16-dione (9)
Δ5-Androstene-3β,16α,17β-triol,7-one (10)

and derivatives thereof wherein one or more of the hydroxyl or keto substituents is a group convertible thereto by hydrolysis.

Examples of such hydrolyzable groups include hydroxyl groups esterified with an acid selected from the group consisting of (i) normal or branched, saturated or unsaturated $C_{2-22}$ aliphatic acids, (ii) $C_{7-12}$ aromatic acids, (iii) $C_3$ or larger dicarboxylic acids in which only one of the carboxyl groups is esterified to the hydroxyl group(s) on the steroid, and (iv) inorganic acids such as sulfuric and phosphoric.

These steroids may also be administered as a carbamate or other such derivative capable of releasing the specified steroid within the intestinal tract, blood and/or body tissue. The desired biological activity is a function of the steroid moiety. Derivations of a moiety may serve a variety of beneficial functions including stabilization of the steroid, flavoring or obscuring the natural flavor of the steroid, or affecting the rate of absorption of the steroid.

Synthesis (1) Δ5-Androstene-3β,7α-diol-17-one (7α-hydroxy DHEA)
Δ5-Androstene-3β,7α-diol-17-one (7α-hydroxy DHEA) can be synthesized from commercially available DHEA acetate by sequentially synthesizing:
Δ5-androstene-3β hydroxy-17-one acetate (DHEA acetate)
Δ5-androstene-3β-hydroxy-7-bromo-17-one acetate (7-Br DHEA acetate)
Δ5-androstene-3β,7α-dihydroxy-17-one diacetate (7-OH DHEA diacetate)

Δ5-androstene-3β,7α-dihydroxy-17-one (7-hydroxy DHEA)

Δ5-Androstene-3β-hydroxy-7-bromo-17-one acetate (7-bromo DHEA acetate) can be synthesized from Δ5-androstene-3β-hydroxy-17-one acetate (DHEA acetate) by reacting DHEA acetate with a brominating agent, such as dibromantin (1,3-dibromo-5,5-dimethylhydantoin) or N-bromosuccinimide. The 7-bromo DHEA acetate is unstable and must be used immediately in the next step of the process.

The 7-bromo DHEA acetate contains an isomeric mixture of 7α-bromo and 7β-bromo. The isomeric mixture, may be equilibrated to 7α-bromo DHEA acetate in accordance with the method described for equilibrating a cholesterol derivative in Confalone, P. N., Kulesha, I. D., and Uskokovic, M. R. *Jour. Org. Chem.*, vol. 46, pp 1030–1032 (1981). Briefly, the isomeric mixture of 7-bromo DHEA acetate is contacted with cold anhydrous LiBr and shielded from light to convert the product from an isomeric mixture of 7α and 7β to predominently 7α.

Δ5-Androstene-3β,7α-dihydroxy-17-one diacetate (7-hydroxy DHEA diacetate) may be synthesized from 7-bromo DHEA acetate by reacting the 7-bromo DHEA acetate with a mixture of glacial acetic acid and powdered silver acetate at room temperature in a suitable solvent, such as a mixture of methylene chloride and acetone.

Δ5-Androstene-3β,7α-dihydroxy-17-one (7-hydroxy DHEA) may be synthesized from 7-hydroxy DHEA diacetate by dissolving the 7-hydroxy DHEA diacetate in methanol and reacting the dissolved 7-hydroxy DHEA diacetate with an aqueous solution containing a suitable base such as $Na_2CO_3$.

The synthesized 7-hydroxy DHEA may then be purified by (i) evaporating the methanol in vacuo, (ii) extracting the 7-hydroxy DHEA into an appropriate organic solvent such as dichloromethane, (iii) evaporating the organic solvent in vacuo, (iv) azeotropically drying the extracted solids containing the 7-hydroxy DHEA with a suitable organic solvent such as ethanol, (v) dissolving the extracted solids in acetone, and then (vi) adding hexane to the acetone solution to produce purified crystals of Δ5-androstene-3β,7α-diol-17-one (7-hydroxy DHEA).

A second crop of Δ5-androstene-3β,7α-diol-17-one (7α-hydroxy DHEA) crystals may be obtained by cooling the resultant solution below room temperature.

(2) Δ5-Androstene-3β-ol-7,17-dione (7-keto DHEA)

Δ5-Androstene-3β-ol-7,17-dione (7-keto DHEA) can be synthesized from commercially available DHEA acetate by sequentially synthesizing:

3β-acetoxy-Δ5-androstene-17-one (DHEA acetate)
3β-acetoxy-Δ5-androstene-7,17 dione (7-one DHEA acetate)
Δ5-androstene-3β-hydroxy-7,17-dione (7-one DHEA)

3β-Acetoxy-Δ5-androstene-7,17-dione (7-one DHEA acetate) can be synthesized from 3β-acetoxy-Δ5-androstene-17-one (DHEA acetate) by reacting the DHEA acetate with the oxidizing agent $CrO_3$ in accordance with the procedure outlined in Fieser, L. F., *Jour. Am. Chem. Soc.*, vol 75, pp 4386–4394 (1953).

Δ5-Androstene-3β-hydroxy-7,17-dione (7-one DHEA) can be synthesized from the 7-one DHEA acetate and purified by employing the deesterification and purification steps set forth above in connection with the synthesis and purification of 7-hydroxy DHEA.

(3) Δ5-Androstene-3β,7α,17β-triol (7α-hydroxy-androstenediol)

Δ5-Androstene-3β,7α,17β-triol (3) can be synthesized from commercially available androstenediol-diacetate by sequentially synthesizing:

Δ5-androstene-3β,17β-diol-diacetate (20)
Δ5-androstene-3β,17β-diol-7-bromo-diacetate (21)
Δ5-androstene-3β,7α,17β-triol-3,7,17-triacetate (22)
Δ5-androstene-3β,7α,17β-triol (3)

Δ5-Androstene 3β,17β-diol-7-bromo-diacetate (21) can be synthesized from the commercially available Δ5-androstene-3β,17β-diol-diacetate (20) by reacting (20) with a brominating agent, such as Dibromantin (1,3-dibromo-5,5-dimethylhydantoin) or N-bromosuccinimide. The synthesized 7-bromo-androstenediol diacetate (21) is unstable and must be used immediately.

The 7-bromo-androstenediol diacetate (21) contains an isomeric mixture of 7α-bromo-androstenediol diacetate (21a) and 7β-bromo-androstenediol diacetate (21b) which can be equilibrated to a 7α-bromo-androstenediol (21a) in accordance with the method described in Confalone, P. N. Kulesha, I. D., and Uskokovic, M. R. *Jour. Org. Chem.*, vol. 46, pp 1030–1032 (1981). Briefly, the isomeric mixture of 7-bromo-androstenediol diacetate (21a & 21b) is contacted with anhydrous LiBr and shielded from light to convert the product from an isomeric mixture of 7α and 7β to predominently 7α.

Δ5-Androstene-3β,7α,17β-triol-3,7,17-triacetate (22) may be synthesized from the 7α-bromo-androstenediol diacetate (21a) by reacting (21a) with a mixture of glacial acetic acid and silver acetate in a suitable solvent, such as a mixture of methylene chloride and acetone.

Δ5-Androstene-3β,7α,17β-triol (3) may be synthesized from the 7α-hydroxy-androstenediol triacetate (22) by reacting the 7α-hydroxy-androstenediol triacetate (22) in methanol with an aqueous solution containing a suitable base such as $Na_2CO_3$.

The synthesized 7α-hydroxy-androstenediol (3) may then be purified by (i) evaporating the methanol in vacuo, (ii) extracting the 7α-hydroxy-androstenediol (3) into an appropriate organic solvent such as dichloromethane, (iii) evaporating the organic solvent in vacuo, (iv) azeotropically drying the extracted solids containing the 7α-hydroxy-androstenediol (3) with a suitable organic solvent such as ethanol, (v) dissolving the extracted solids in acetone, and then (vi) adding hexane to the acetone solution to produce purified crystals of Δ5-androstene-3β,7α,17β-triol (7α-hydroxy-androstenediol) (3).

A second crop of Δ5-androstene-3β,7α,17β-triol (3) crystals may be obtained by cooling the resultant solution below room temperature.

(4) Δ5-Androstene-3β,17β-diol-7-one (7-keto-androstenediol)

Δ5-Androstene-3β,17β-diol-7-one (4) can be synthesized from commercially available androstenediol-diacetate by sequentially synthesizing:

Δ5-androstene-3β,17β-diol-7-one-diacetate (41)
Δ5-androstene-3β,17β-diol-7-one (4)

Δ5-Androstene-3β,17β-diol-7-one-diacetate (41) can be synthesized from Δ5-androstene-3β,17β-diol-diacetate (androstenediol-diacetate) (40) by reacting the androstenediol-diacetate (40) with the oxidizing agent $CrO_3$ in accordance with the procedure outlined in Fieser, L. F. *Jour. Am. Chem. Soc.*, vol. 75, pp 4386–4394 (1953).

Δ5-Androstene-3β,17β-diol-7-one (7-keto-androstenediol) (4) can be synthesized from Δ5-androstene-3β,17β-diol-7-one-diacetate (41) and purified by employing the deesterification and purification steps set forth above with respect to the synthesis and purification of 7α-hydroxy DHEA (1) from 7α-hydroxy DHEA diacetate.

(5) Δ5-Androstene-3β-acetoxy-7,16,17-trione

Δ5-Androstene-3β-acetoxy-7,16,17-trione (5) may be synthesized from commercially available DHEA acetate by sequentially converting:

---

3β-acetoxy-Δ5-androstene-17-one (DHEA-acetate)
- to -
3β-acetoxy-Δ5-androstene-7,17-dione   (51)
- to -

| 3β-acetoxy-17-hydroxy-Δ5, Δ16-androstadiene-7-one - trimethylsilyl ether (52a) 30% | 3β-trimethylsilylacetoxy-17-hydroxy-Δ5,Δ16-androstadiene-7-one trimethylsilyl ether (52b) 70% |
|---|---|

- to -

| 3β-acetoxy-trimethylsilylacetoxy-16-phenylseleno-Δ5-androstene-7,17-dione (53b) | 3β-16-phenylseleno-Δ5-androstene-7,17-dione (53a) |
|---|---|

| phenylseleno- (53a) | - to - 3β-acetoxy-16-Δ5-androstene-7,17-dione |
|---|---|

- to -

| 3β-acetoxy-Δ5-androstene-16-phenylseleno-16-m-chlorobenzoate-dione 7,17-dione (54) | 3β,16-diacetoxy-Δ5-androstene-16-phenylseleno-7,17- (55) |
|---|---|

- to -

| 3β-acetoxy-16-m chlorobenzoate-Δ5,Δ15-dione androstadiene-7,17-dione (56) | 3β,16-diacetoxy-Δ5,Δ15-androstadiene-7,17- (57) |
|---|---|

- to -
3β-acetoxy-Δ5-androstene-7,16,17-trione (5)

---

3β-Acetoxy-Δ5-androstene-7,17-dione (51) can be synthesized from 3β-acetoxy-Δ5-androstene-17-one (DHEA-acetate) by reacting DHEA-acetate with the oxidizing agent $CrO_3$ in accordance with the procedure outlined in Fieser, L. F., *Jour. Am. Chem. Soc.*, vol. 75, pp 4386–4394 (1953).

A mixture of 70% 3β-(trimethylsilyl)acetoxy-17-hydroxy-Δ5,Δ16-androstadiene-7-one trimethylsilyl ether (52b) and 30% 3β-acetoxy-17-hydroxy-Δ5,Δ16-androstadiene-7-one trimethylsilyl ether (52a) may be synthesized from the 3β-acetoxy-Δ5-androstene 7,17-dione (51) by reacting (51) with lithium diisopropyl amide in the presence of trimethylchlorosilane in a suitable solvent such as tetrahydrofuran at −78° C.

3β-Acetoxy-16-phenylseleno-Δ5-androstene-7,17-dione (53a) and 3β-(trimethylsilyl)acetoxy-16-phenylseleno-Δ5-androstene-7,17-dione (53b) may be synthesized from 3β-acetoxy-17-hydroxy-Δ5,Δ16-androstadiene-7-one trimethylsilyl ether (52a) and 3β-(trimethylsilyl)acetoxy-17-hydroxy-Δ5,Δ16-androstadiene-7-one trimethylsilyl ether (52b) respectively by reacting the mixture of (52a) and (52b) with benzeneselenenyl chloride in the presence of pyridine and a suitable solvent such as tetrahydrofuran at −78° C.

The carbon silyated acetate attached to the $C_3$ carbon atom on the (53b) fraction of the (53) mixture may be desilylated so as to convert (53b) to (53a) within the (53) mixture by treating the (53) mixture with tetra-n-butylammonium fluoride in a suitable solvent system such as ether-dichloromethane-tetrahydrofuran-water.

3β,16-Diacetoxy-Δ5-androstene-16-phenylseleno-7,17-dione (54) may be synthesized from the 3β-acetoxy-16-phenylseleno-Δ5-androstene-7,17-dione (53a) by submitting (53a) to the seleno-Pummerer reaction outlined in Ikota, N.; Ganem, B. *Jour. Org. Chem.*, vol. 43, pp. 1607–1608 (1978). Briefly, the 3β-acetoxy-16-phenylseleno-Δ5 -androstene-7,17-dione (53a) is sequentially reacted with m-chloroperbenzoic acid and acetic anhydride in a suitable solvent. 3β-acetoxy-Δ5-androstene-16-phenylseleno-16-m-chlorobenzoate-7,17-dione (54) is also synthesized during this reaction.

3β,16-diacetoxy-Δ5,Δ15-androstadiene-7,17-dione (57) may be synthesized from 3β,16-diacetoxy-Δ5-androstene-16-phenylseleno-7,17-dione (55) by oxidative dehydrogenation. The 3β-acetoxy-Δ5-androstene-16-phenylseleno-16-m-chlorobenzoate-7,17-dione (54) present with (55) produces 3β-acetoxy-16-m-chlorobenzoate-Δ5,Δ15-androstadiene-7,17-dione (56) which may be separated by chromatography if desired.

3β-acetoxy-Δ5-androstene-7,16,17-trione (5) may be synthesized from the 3β-acetoxy-Δ5,Δ15 androstadiene-16-m-chlorobenzoate-7,17-dione (56) and/or 3β,16-diacetoxy-Δ5,Δ15-androstadiene-7,17-dione (57) by treating them with triethylamine in methanol.

(6) Δ5-Androstene-3β,16α-dihydroxy-7,17-dione (7-keto-16α-hydroxy DHEA)

3β,16α-dihydroxy-Δ5-androstene-7,17-dione can be synthesized by the following sequence from DHEA propionate. DHEA propionate can be made by simple esterification of DHEA.

---

3β-propionoxy-Δ5-androstene-17 one   (DHEA-propionate)
- to -
3β-propionoxy-Δ5-androstene-7,17-dione (61)
- to -
3β-propionoxy-17-hydroxy-Δ5,Δ16-androstadiene-7-one trimethylsilyl ether   (62)
- to -
3β-propionoxy-16α-hydroxy-Δ5-androstene-7,17-dione   (63)
- to -
3β,16α-dihydroxy-Δ5-androstene-7,17-dione (6)

---

3β-Propionoxy-Δ5-androstene-7,17-dione (61) (NMR set forth at table eight) can be synthesized from 3β-propionoxy-Δ5-Androstene-17-one (DHEA-propionate) by reacting the DHEA-propionate with the oxidizing agent $CrO_3$ in accordance with the procedure outlined in Fieser, L. F., *Jour. Am. Chem. Soc.*, vol. 75, pp 4386–4394 (1953).

3β-Propionoxy-17-hydroxy-Δ5,Δ16-androstadiene-7-one trimethylsilyl ether (62) may be synthesized from the 3β-propionoxy-Δ5-androstene-7,17-dione (61) by reacting (61) with lithium diisopropyl amide in the presence of trimethylchlorosilane in a suitable solvent such as tetrahydrofuran at −78° C.

3β-Propionoxy-16α-hydroxy-Δ5-androstene-7,17-dione (63) may be synthesized from the 3β-propionoxy-17-hydroxy-Δ5,Δ16-androstadiene-7-one trimethylsilyl ether (62) by oxidation with m-chloroperbenzoic acid in tetrahydrofuran followed by treatment with a 1N HCl solution.

The final desired product 3β,16α-dihydroxy-Δ5-androstene-7,17-dione (6) may then be synthesized from the 3β-propionoxy-16α-hydroxy-Δ5-androstene-7,17-dione (63) by treatment with sulfuric acid in methanol.

(7) Δ5-Androstene-3β-propionoxy, 16β-acetoxy-7,17 -dione (7-Keto-16β-acetoxy DHEA propionate)

Δ5-Androstene-3β-propionoxy-16β-acetoxy-7,17-dione (7) can be synthesized from Δ5-androstene-3β-propionoxy-16α-hydroxy-7,17-dione (63) produced in accordance with the reaction sequence set forth above. The Δ5-androstene-3β-propionoxy-16α-hydroxy-7,17-dione is treated in accordance with the Mitsunobu conditions set forth in Hughes, D. L.; Reamer, R. A.; Bergan, J. J.; Grabowski, E. J. J. *Jour Am. Chem. Soc.*, vol. 110, pp 6487–6491 to invert the configuration and acetylate the 16 hydroxy group.

(8) Δ5-Androstene-3β,7α,17β-triol-16-one

Δ5-Androstene-3β,7α,17β-triol-16-one (8) can be synthesized from Δ5-androstene-3β,16α-dihydroxy-17-one diacetate (81). The Δ5-androstene-3β,16α-dihydroxy-17-one diacetate (81) starting material can be synthesized in accordance with the procedure set forth in Numazawa, M. and Osawa, Y. *Steroids*, vol. 32, p 519 (1978).

Δ5-Androstene-3β,16α-diacetoxy-7-bromo-17-one (82) can be synthesized from the Δ5-androstene-3β,16α-diacetoxy-17-one (81) by reacting Δ5-androstene-3β,16α-diacetoxy-17-one (81) with a brominating agent, such as Dibromantin (1,3-dibromo-5,5-dimethylhydantoin). The Δ5-androstene-3β,16α-diacetoxy-7-bromo-17-one (82) is unstable and must be used immediately in the next step of the process.

The Δ5-androstene-3β,16α-diacetoxy-7-bromo-17-one (82) contains an isomeric mixture of 7α-bromo and 7β-bromo isomers. The isomeric mixture, may be equilibrated to 7α-bromo in accordance with the method described for equilibriating a cholesterol derivative in Confalone, P. N., Kulesha, I. D., and Uskokovic, M. R. *Jour. Org. Chem.*, vol. 46, pp 1030–1032 (1981). Briefly, the isomeric mixture is contacted with cold anhydrous LiBr and shielded from light to convert the product from an isomeric mixture of 7α and 7β to predominently 7α.

Δ5-Androstene-3β,16α-diacetoxy-7α-hydroxy-17-one (83) may be synthesized from the Δ5-androstene-3β,16α-diacetoxy-7α-bromo-17-one (82) by reacting the Δ5-androstene-3β,16α-diacetoxy-7α-bromo-17-one (82) with a mixture of glacial acetic acid and powdered silver acetate at room temperature in a suitable solvent, such as a mixture of methylene chloride and acetone. Also produced in this reaction is a 20% yield of Δ5-androstene-3β,7α,16α-triacetoxy-17-one.

Δ5-Androstene-3β,7α,17β-trihydroxy-16-one (8) can be synthesized from the Δ5-Androstene-3β,16α-diacetoxy-7α-hydroxy-17-one (83) by dissolving the Δ5-Androstene-3β,16α-diacetoxy-7α-hydroxy-17-one (83) in a room temperature methanol solution of $K_2CO_3$ and stirring the solution for two hours. The alkaline solution enolizes the 17-keto to form the more stable 17-hydroxy-16-one combination. The Δ5-androstene-3β,7β,17-trihydroxy-16-one (8) may then be isolated by filtering to remove the insoluble salt, evaporating the methanol in vacuo, purifying and remove extracting the compound by chromatography. The steroid crystallizes from a hot methanol/ether solution upon cooling.

(9) Δ5-Androstene-3β,17β-diol-7,16-dione

Δ5-Androstene-3β,17β,-diol-7,16-dione (9) can be synthesized from 3β-propionoxy-16α-hydroxy-Δ5-androstene-7,17-dione (63) by treating 3β-propionoxy-16α-hydroxy-Δ5-androstene-7,17-dione (63) with a 5% aqueous sodium carbonate solution in methanol.

(10) Δ5-Androstene-3β,16α,17β-triol,7-one

Δ5-Androstene-3β,16α,17β-triol-7-one (10) can be synthesized from 3β,16α,17β-triacetoxy-Δ5-androstene by reacting the 3β,16α,17β-triacetoxy-Δ5-androstene with the oxidizing agent $CrO_3$ in accordance with the procedure outlined in Fieser, L. F., *Jour. Am. Chem. Soc.*, vol 75, pp 4386–4394 (1953) with subsequent hydrolysis of the acetyl groups.

Without intending to be unduly limited thereby, it is believed that the steroids identified above may be modified without loss of biological activity by esterifying one or more of the hydroxyl groups with any of a variety of organic acids and inorganic acids such as sulfuric or phosphoric acid.

Treatment

A subject may be treated with the steroids specified herein by any of the commonly accepted practices including orally or by injection. While many factors affect the dose rate required to attain the desired biological response, treatment at a dosage rate of about 0.1 to 2 grams, preferably about 0.5 to 2 grams, of the steroid per 100 kilograms body weight per day should generally be effective for promoting weight control. A dose rate of less than 0.1 gram per 100 kilograms bodyweight per day is generally ineffective for preventing weight gain while a dose rate of greater than about 2 grams per 100 kilograms bodyweight per day increases the cost of treatment without providing a corresponding benefit in performance. The optimum dose rate to be administered to a subject is case specific as the optimum dose rate depends upon several factors including current body composition (percent fat), the desired effect (weight gain maintenance versus weight loss), eating habits of the individual (daily caloric intake), and the like. As would be expected, the dose rate provided to a subject for the purpose of promoting weight loss will be greater than that necessary to promote weight maintenance assuming identical caloric intake under each program.

Without intending to be limited thereby, we believe that the steroids specified herein are metabolic intermediates along the pathway to conversion of DHEA to an ultimate metabolite(s) which is actually responsible for mediating an enhanced production of thermogenic enzymes such as glycerol 3-phosphate dehydrogenase and malic enzyme.

A subject may be treated with one of the steroids specified herein on substantially any time schedule. It is believed that the steroids specified herein are effective for promoting weight control while the steroid itself is actively present within the body as well as while the increased concentration of thermogenic enzyme(s) induced by the steroid remain elevated. The in vivo life expectancy of the steroids and the thermogenic enzyme(s) induced thereby is not yet fully known. However, it is believed that the steroids themselves are not stored within the body and are removed and/or deactivated within days after administration. Accordingly, for optimum effectiveness, the subject under treatment should be treated every day or two. For reasons of convenience the subject under treatment may be treated less frequently, such as once a week, when less than maximum performance is acceptable.

As is apparent from the factors which affect dosage and dose rate, each particular subject should be carefully and frequently reviewed and the dosage and/or dose rate altered in accordance with the particular situation.

Experimental

Example I
(Steroid 1)

Synthesis

Δ5-Androstene-3β,7α-diol-17-one (Step 1) Into a two liter, triple neck, round bottom flask equipped with a magnetic stirrer and a reflux condenser was placed 1000 ml hexane (b.p 69°–71°), 10 grams (0.03 mmoles) DHEA acetate and 13.6 grams (0.16 moles) $NaHCO_3$ to form a first mixture. The first mixture was placed under a $N_2$ atmosphere and heated under constant agitation to reflux. Into the refluxing first mixture was added 6.11 grams (0.021 moles) Dibromantin (1,3-dibromo-5,5-dimethylhydantoin) as a brominating agent to form a second mixture. The second mixture gradually turned orange after which it rapidly turned a pale white/yellow. The second mixture was refluxed for 30 minutes, cooled to room temperature and filtered through a sintered glass funnel. The residue was rinsed with 50 ml dichloromethane and the combined filtrate rotovapped to dryness at a temperature of less than 35° C. The residue (Δ5-androstene-3β-ol-7-bromo-17-one) is unstable to storage and was used immediately in step two.

(Step 2) The residue was resolubilized in 80 ml of dichloromethane in a one liter stoppered flask equipped with a magnetic stirrer and placed in an ice bath. Into the resolubilized filtrate was added 8 grams anhydrous LiBr in 320 ml ice-cold acetone to form a third mixture. The third mixture was shielded from light and stirred continuously for three hours. The resulting mixture containing predominantly Δ5-androstene-3β-ol-7α-bromo-17-one was allowed to warm to room temperature and used immediately in step three.

(Step 3) Into a 500 ml flask equipped with a magnetic stirrer was placed 320 ml dichloromethane, 80 ml glacial acetic acid, and 26 grams of silver acetate to form a first suspension. The first suspension was stirred continuously for 20 minutes at room temperature. The stirred first suspension was added under constant agitation into the third mixture of predominantly Δ5-androstene-3β-ol-7α-bromo-17-one to form a second suspension. The second suspension was constantly stirred for 30 minutes at room temperature after which the suspension was filtered through a sintered glass funnel to separate a solid residue. The filtered solid residue was rinsed with 100 ml dichloromethane. The filtrate was washed three times with 1000 ml of water, once with 1000 ml of a 5% NaHCO$_3$ solution, and then twice more with water. The organic mixture containing Δ5-androstene-3β-17α-diol-17-one diacetate was then rotovapped to dryness.

(Step 4) The dried extracted solids were resolubilized in 500 ml methanol in a one liter, triple necked flask equipped with a magnetic stirrer and a reflux condenser to form a fourth mixture. The fourth mixture was placed under a N$_2$ atmosphere and heated under constant stirring to reflux. Into the fourth mixture was added 250 ml of a 5% aqueous solution of Na$_2$CO$_3$ to form a fifth mixture. The fifth mixture was refluxed under constant agitation for 45 minutes. The methanol was rotovapped off and the aqueous fifth mixture carefully brought to a pH of 7 with an appropriate amount of glacial acetic acid. The neutralized fifth mixture was extracted twice with 100 ml of dichloromethane. The dichloromethane solution of Δ5-androstene-3β,7α-diol-17-one was rotovapped to near dryness, azeotropically dried with absolute ethanol, and then azeotropically dried twice with acetone. Warm acetone was added to the dried extracted solids until the solids were completely dissolved to form a sixth mixture. Hexane was added to the sixth mixture until the mixture began to cloud at which time crystals of Δ5-androstene-3β-7α-diol-17-one began to form at room temperature.

A second crop of Δ5-androstene-3β-7α-diol-17-one crystals was obtained by cooling the remaining sixth mixture.

The crystals melt at 187°–189° C. When recrystallized from acetone/hexane they melt at 192°–193° C.

Example II
(Steroid 1)

Synthesis

Δ5-Androstene-3β-7(αβ)-diol-17-one

Δ5-Androstene-3β-7(αβ)-diol-17-one was manufactured in accordance with the procedure set forth in Example I except that Step 2 was eliminated with the dried filtrate from Step 1 simply resolubilized in the 80 ml of dichloromethane in preparation for Step 3.

Example III
(Steroid 2)

Synthesis

Δ5-Androstene-3β-ol-7,17-dione (Step 1) Into a 50 ml flask equipped with a magnetic stirrer and a water bath was placed 6.5 ml acetic anhydride, 23 ml acetic acid, 1.7 grams sodium acetate, and 2 grams DHEA acetate to form a first mixture. Into tile first mixture was added 2 grams chromium trioxide over a thirty minute period to form a second mixture. The first mixture was maintained at a constant temperature of 56°–58° C. and continuously agitated during addition of the chromium trioxide. The second mixture was maintained at 56°–58° C. and continuously agitated for an additional hour after which the second mixture was cooled and slowly poured under continuous agitation into 600 ml of ice water to form a precipitate. The flocculent precipitate was collected on a sintered glass funnel and washed with water until no longer green. After drying in vacuo over P$_2$O$_5$ the product was dissolved in hot methanol and crystallized to yield substantially pure Δ5-androstene-3β-acetoxy-7,17-dione having a melting point of 184°–185° C.

(Step 2) The precipitate was resolubilized in 500 ml of methanol in a one liter, triple necked, round bottom flask equipped with a magnetic stirrer and reflux condenser to form a third mixture. The third mixture was placed under a N$_2$ atmosphere and heated under constant agitation to reflux. Into the third mixture was added 250 ml of a 5% solution of Na$_2$CO$_3$ to form a fourth mixture. The fourth mixture was refluxed under constant agitation for 45 minutes. The methanol was rotovapped off and the aqueous fourth mixture carefully brought to a pH of 7 with an appropriate amount of glacial acetic acid. The neutralized fourth mixture was extracted with two 100 ml portions of dichloromethane, the two dichloromethane portions combined, and the dichloromethane evaporated in vacuo. The extracted solids were then azeotropically dried first with absolute ethanol and then with two separate portions of acetone. Methanol was added to the dried extracted solids until the solids were completely dissolved to form a fifth mixture. Hexane was added to the fifth mixture until the mixture began to cloud at which time crystals of Δ5-androstene-3β-ol-7,17 dione formed at room temperature.

A second crop of Δ5-androstene-3β-ol-7,17-dione crystals was obtained by cooling the remaining sixth mixture.

The resultant product had a melting point of 235°–238° C.

Example IV
(Steroid 3)

Synthesis

Δ5-Androstene-3β,7α,17β-triol (Step 1) Into a two liter round bottom flask equipped with a magnetic stirrer and a reflux condenser was placed 1000 ml hexane (b.p 69°–71°), 10 grams (0.03 moles) Δ5-androstene-3β-17β-diol diacetate and 13.6 grams (0.16 moles) NaHCO$_3$ to form a first mixture. The first mixture was placed under a N$_2$ atmosphere and heated under constant agitation to reflux. Into the refluxing first mixture was added 6.11 g (0.021 moles) Dibromantin (1,3-dibromo-5,5-dimethylhydantoin) as a brominating agent to form a second mixture. The second mixture gradually turned orange after which it rapidly turned a pale white/light yellow. The second mixture was refluxed for 30 minutes, cooled to room temperature, and filtered through a sintered glass funnel. The residue was rinsed with 50 ml dichloromethane and rotovapped to dryness at a temperature of less than 35° C. The dry filtrate (Δ5-androstene-3β-17β-diol-7-bromide) is unstable to storage and was used immediately in step two.

(Step 2) The dried filtrate was resolubilized in 80 ml of dichloromethane in a flask equipped with a magnetic stirrer and placed in an ice bath. Into the resolubilized filtrate was added 8 grams anhydrous LiBr in 320 ml ice-cold acetone to form a third mixture. The third mixture was shielded from light and stirred continuously for three hours. The resulting mixture of predominantly Δ5-androstene-3β-17β-diol-7α-bromide was allowed to warm to room temperature and used immediately.

(Step 3) Into a 500 ml flask equipped with a magnetic stirrer was placed 320 ml methylene chloride, 80 ml glacial acetic acid, and 26 grams silver acetate to form a first suspension. The first suspension was stirred continuously for 20 minutes at room temperature. The stirred first suspension was added under constant agitation to the third mixture of predominantly Δ5-androstene-3β-17β-diol-7α-bromide to form a second suspension. The second suspension was constantly stirred for 30 minutes at room temperature during which the suspension gradually darkened and was then filtered through a sintered glass funnel. The residual solids retained on the glass filter were rinsed with 10 ml dichloromethane. The filtrate was washed three times with 1000 ml of water, neutralized with 1000 ml of a 5% $NaHCO_3$ solution, and then washed twice more with water. The resulting organic mixture containing Δ5-androstene-3β,7α,17β-triol-3,17-diacetate was then rotovapped to dryness.

(Step 4) The dried extracted solids were resolubilized in 500 ml methanol within in a one liter, triple necked, round bottom flask equipped with a magnetic stirrer and a reflux condenser to form a fourth mixture. The fourth mixture was placed under a $N_2$ atmosphere and heated under constant agitation to reflux. Into the fourth mixture was added 250 ml of a 5% aqueous solution of $Na_2CO_3$ to form a fifth mixture. The fifth mixture was refluxed under constant agitation for 45 minutes. The methanol was rotovapped off and the aqueous fifth mixture carefully brought to a pH of 7 with an appropriate amount of glacial acetic acid. The neutralized fifth mixture was extracted twice with 100 ml dichloromethane and the combined extract evaporated in vacuo. The extracted solids (Δ5-androstene-3β,7α,17β-triol) were azeotropically dried with absolute ethanol and then twice with acetone. Warm acetone was added to the dried extracted solids until the solids were completely dissolved to form a sixth mixture. Hexane was added to the sixth mixture until the mixture began to cloud, at which time crystals of Δ5-androstene-3β,7α,17β-triol formed at room temperature.

A second crop of Δ5-androstene-3β,7α,17β-triol crystals was obtained by cooling the remaining sixth mixture.

Example V
(Steroid 3)

Synthesis

Δ5-Androstene-3β,7(αβ),17β-triol

Δ5-Androstene-3β,7(αβ),17β-triol was manufactured in accordance with the procedure set forth in Example IV except that Step 2 was eliminated with the dried filtrate from Step 1 simply resolublized in the 80 ml of methylene chloride in preparation for Step 3.

Example VI
(Steroid 4)

Synthesis

Δ5-Androstene-3β,17β-diol-7-one (Step 1) Into a 50 ml flask equipped with a magnetic stirrer and a water bath was placed 6.5 ml acetic anhydride, 23 ml acetic acid, 1.7 grams sodium acetate, and 2 grams androstenediol diacetate to form a first mixture. Into the first mixture was added 2 grams chromium trioxide over a thirty minute period to form a second mixture. The first mixture was maintained at a constant temperature of 56°–58° C. and continuously agitated during addition of the chromium trioxide. The second mixture was maintained at 56°–58° C. and continuously agitated for an additional hour after which the second mixture was cooled and slowly poured with continuous agitation into 600 ml of ice water to form a precipitate. The flocculent precipitate was filtered through a sintered glass funnel, washed with water until no longer green, and dried in vacuo.

(Step 2) The dried precipitate was resolubilized in 500 ml of methanol in a one liter, round bottom flask equipped with a magnetic stirrer and reflux condenser to form a third mixture. The third mixture was placed under a $N_2$ atmosphere and heated under constant agitation to reflux. Into the third mixture was added 250 ml of a 5% aqueous solution of $Na_2CO_3$ to form a fourth mixture. The fourth mixture was refluxed under constant agitation for 45 minutes. The methanol was rotovapped off and the aqueous fourth mixture carefully brought to a pH of 7 with an appropriate amount of glacial acetic acid. The neutralized fourth mixture was extracted twice with 100 ml portions of dichloromethane and the combined dichloromethane extract evaporated in vacuo. The extracted solids were then azeotropically dried first with absolute ethanol and then twice with acetone. Methanol was added to the dried extracted solids until the solids were completely dissolved to form a fifth mixture. Hexane was added to the fifth mixture until the mixture began to cloud at which time crystals of Δ5-androstene-3β, 17β-diol-7-one formed at room temperature.

The resultant product had a melting point of 200°–202° C.

Example VII
(Steroid 5)

Synthesis

Δ5-Androstene-3β-acetoxy-7,16,17-trione (Step 1) Into a 50 ml flask equipped with a magnetic stirrer and a water bath was placed 6.5 ml acetic anhydride, 23 ml acetic acid, 1.7 grams sodium acetate, and 2 grams DHEA acetate to form a first mixture. Into the first mixture was added 2 grams chromium trioxide over a thirty minute period to form a second mixture. The first mixture was maintained at a constant temperature of 56°–58° C. and continuously agitated during addition of the chromium trioxide.

(Step 2) The second mixture was maintained at 56°–58° C. and continuously agitated for an additional hour after which the second mixture was cooled and slowly poured under continuous agitation into 600 ml of ice water to form a precipitate. The flocculent precipitate was collected on a sintered glass funnel and washed with water until no longer green. After drying in vacuo over $P_2O_5$, the product was dissolved in methanol and recrystallized to yield substantially pure 3β-acetoxy-Δ5-androstene-7,17-dione (51) having a melting point of 184°–185° C.

(Step 3) Into a second 50 ml round bottom flask equipped with a magnetic stirrer and retained within a dry-ice bath was placed 1.00 gram (2.90 mmoles) of the 3β-acetoxy-Δ5-androstene-7,17-dione (51) and 20 ml neat tetrahydrofuran to form a third mixture. The third mixture was placed under a $N_2$ atmosphere. Into the third mixture was added 1.07 ml (8.43 mmoles) trimethylchlorosilane to form a fourth mixture. The fourth mixture was maintained under the $N_2$ atmosphere and cooled to −78° C.

(Step 4) Into a third 25 ml round bottom flask equipped with a magnetic stirrer and retained within a dry-ice bath was placed 1.07 ml (7.66 mmoles) diisopropyl amine, 3.60 ml of a 1.94M solution of n-butyllithium in hexane (6.96 mmoles), and 4 ml of tetrahydrofuran to form lithium diisopropyl amide. The solution (LDA solution) was prepared under a $N_2$ atmosphere at −78° C. The LDA solution was warmed slightly to dissolve any solids therein and then added, under a $N_2$ atmosphere, to the fourth mixture via cannula to form a fifth mixture.

(Step 5) The fifth mixture was removed from the dry-ice bath and allowed to warm to room temperature for 15 minutes at which time 1.25 ml triethylamine was added to the fifth mixture to form a sixth mixture. Into a separatory funnel was placed 40 ml hexane, 40 ml of a saturated $NaHCO_3$ aqueous solution, and the sixth mixture. The organic phase was extracted with hexane, washed with a saturated NaCl aqueous solution, dried over $Na_2SO_4$ and the solvent removed to yield 1.42 grams of a dry organic solid. The organic solid was identified by NMR ($CDCl_3$) as an approximately 70:30 mixture of 3β-(trimethylsilyl)acetoxy-17-hydroxy-Δ5,Δ16-androstadiene-7-one trimethylsilyl ether (52b) and 3β-acetoxy-17-hydroxy-Δ5,Δ16-androstadiene-7-one trimethylsilyl ether (52a). The results of the NMR analysis are set forth in Tables One & Two.

(Step 6) Into a fourth 100 ml round bottom flask equipped with a magnetic stirrer and retained within a dry-ice bath was placed 2.85 mmoles of the organic solid obtained in Step 5, 20 ml neat tetrahydrofuran and 0.320 ml (4.00 mole) neat pyridine to form a seventh mixture. The seventh mixture was cooled to −78° C. and placed under a $N_2$ atmosphere. Into the seventh mixture was added 0.710 grams (3.71 moles) of benzeneselenenyl chloride in 4 ml of tetrahydrofuran to form an eighth mixture.

(Step 7) Into a separatory funnel was placed a cosolvent system of a 0.5N HCl aqueous solution and dichloromethane. Into the cosolvent system was added the eighth mixture to extract the organic phase. The second organic phase was extracted by dichloromethane, sequentially washed with water and a saturated $NaHCO_3$ aqueous solution, dried over $Na_2SO_4$ and the solvent removed to yield 1.72 grams of an organic oil. The organic oil was separated by chromatography (100 grams silica eluted with hexane-ethyl acetate at 90:10 to 50:50 with 50 ml fractions) into 1.44 grams of first and second organic fractions (Fractions 14–17), diphenyl diselenide (Fractions 9–11) and unreacted 3β-acetoxy-Δ5-androstene-7,17-dione (51) (Fractions 18–19). The first and second organic fractions were identified by NMR as 3β-acetoxy-16*-phenylseleno-Δ5-androstene-7,17-dione (53a) and 3β-(trimethylsilyl)acetoxy-16-phenylseleno-Δ5-androstene-7,17-dione (53b) respectively. The results of the NMR analysis are set forth in Tables Three and Four.

(Step 8) Into a fifth 100 ml round bottom flask equipped with a magnetic stirrer was placed 25 ml ether, 5 ml dichloromethane and 1.19 mmoles of the second organic fraction obtained in Step 7 (53b) to form a ninth mixture. Into the ninth mixture was added 8 ml of a 10% aqueous solution of potassium fluoride and 3 ml of a 1M tetra-n-butylammonium fluoride solution in tetrahydrofuran to form a tenth mixture. The tenth mixture was maintained at 25° C. and continuously agitated for two hours after which the tenth mixture was poured into an ether-hexane-water solvent system to extract the organic phase. The extracted organic phase was washed twice with water, once with a saturated NaCl aqueous solution, dried over $Na_2SO_4$ and the solvent removed to yield 0.594 grams of 3β-acetoxy-16-phenylseleno-Δ5-androstene-7,17-dione (53a).

(Step 9) Into a sixth 100 ml round bottom flask equipped with a magnetic stirrer was placed 25 ml dichloromethane and 1.10 mmoles of 3β-acetoxy-16-phenylseleno-Δ5-androstene-7,17-dione (53a) to form an eleventh mixture. The eleventh mixture was cooled to 0° C. and maintained under continuous agitation. Into the eleventh mixture was added 0.296 grams (1.2 mmoles) m-chloroperbenzoic acid (70%) followed five minutes later by 0.40 ml dimethylsulfide to form a thirteenth mixture. The thirteenth mixture was washed 3 times with 50 ml of a cold $NaHCO_3$ aqueous solution and filtered through $Na_2SO_4$.

(Step 10) Into a seventh 250 ml round bottom flask equipped with a magnetic stirrer was placed 1.2 ml acetic anhydride, 1.2 ml pyridine and the liquid phase of the thirteenth mixture to form a fourteenth mixture. The fourteenth mixture was continuously agitated at room temperature for an hour after which 60 ml of a saturated $NaHCO_3$ aqueous solution was added to form a fifteenth mixture having separate organic and inorganic layers. The fifteenth mixture was maintained under continuous agitation until bubbling ceased. The organic layer was separated from the inorganic layer by drawing off the organic layer in a separatory funnel. The separated organic layer was washed with a saturated $NaHCO_3$ aqueous solution, dried over $Na_2SO_4$ and the solvent removed to yield 0.713 grams of a dry organic solid. The organic solid was identified by NMR ($CDCl_3$) as a 90:10 mixture of 3β,16-diacetoxy-16-phenylseleno-Δ5-androstene-7,17-dione (55) and 3β-acetoxy-Δ5-androstene-16-phenylseleno-16-m-chlorobenzoate-7,17-dione (54). The results of an NMR analysis of the (55) fraction in the mixture are set forth in Table Five.

(Step 11) Into a round bottom flask equipped with a magnetic stirrer was placed 25 ml carbon tetrachloride and 1.10 mmoles of the 90:10 mixture of 3β,16-diacetoxy-16-phenylseleno-Δ5-androstene-7,17-dione (55) and 3β-acetoxy-Δ5-androstene-16-phenylseleno-16-m-chlorobenzoate-7,17-dione (54) to form a sixteenth mixture. Into the sixteenth mixture was added 0.12 ml pyridine, 10 mg benzeneseleninic acid, and 19 mg diphenyldiselenide to form a seventeenth mixture. The seventeenth mixture was maintained under vigorous agitation and 3.4 ml of a 15% $H_2O_2$ aqueous solution added to form an eighteenth mixture. The eighteenth mixture was agitated continuously for 45 minutes after which the eighteenth mixture was washed twice with a saturated $NaHCO_3$ aqueous solution and dried in vacuo to yield 0.390 grams of an organic solid. The organic solid was separated by chromatography (50 grams silica gel eluted with 50% hexane-ethyl acetate with 25 ml fractions) to yield 0.236 grams of an organic fraction (Fractions 9–10). The organic fraction was identified by NMR as pure 3β,16-diacetoxy-Δ5,Δ15-androstadiene-7,17-dione (57). The results of the NMR analysis are set forth in Table Six.

(Step 12) Into a round bottom flask equipped with a magnetic stirrer was placed 1.03 mmoles of 3β,16-diacetoxy-Δ5,Δ15-androstadiene-7,17-dione (57) and 15 ml methanol to form a nineteenth mixture. Into the nineteenth mixture was placed 0,500 ml triethylamine to form a twentieth mixture. The twentieth mixture was placed under a $N_2$ atmosphere and maintained under constant agitation for 16 hours. The twentieth mixture was then extracted between $H_2O$ and $CH_2Cl_2$. The organic layer was washed twice with a saturated $NaHCO_3$ aqueous solution, and then dried and evaporated under reduced pressure to yield 0.281 grams of a yellow organic solid. The organic solid was identified by NMR as a mixture of organic compounds including about 65% 3β-acetoxy-Δ5-androstene-7,16,17-trione (5). The results of the NMR analysis are set forth in Table Seven.

Example VIII
(Steroid 6)

Synthesis

3β,16α-Dihydroxy-Δ5-androstene-7,17-dione (Step 1) Into a round bottom flask equipped with a magnetic stirrer was placed 2.80 mmoles of 3β-propionoxy-17-hydroxy-Δ5,Δ16-androstadiene-7-one trimethylsilyl ether (62) synthesized in accordance with the procedure set forth in Example VII and identified by NMR (See Table Nine) and 40 ml of tetrahydrofuran to form a first mixture which was cooled to 0° in an ice bath. Into the first mixture was placed 2.95 mmoles of m-chloroperbenzoic acid (80–90%) to form a second mixture. The second mixture was warmed to 25° C. and maintained under constant agitation for 10 min.

(Step 2) The second mixture was continuously agitated and 40 ml of a 1N HCl aqueous solution added to form a third mixture which was maintained under constant agitation for 20 min. The third mixture was partitioned between ether and water and separated by decanting the ether phase from the water phase. The ether phase was washed with a saturated $NaHCO_3$ aqueous solution, then a saturated NaCl aqueous solution, and dried in vacuo to yield an organic solid. The organic solid was purified by chromatography (140 gm of silica eluted with 60:40 to 70:30 ethyl acetate-hexane with 25 ml fractions) to give 0.586 gm of a first organic compound. The first organic compound was identified by NMR as 3β-propionoxy-16α-hydroxy-Δ5-androstene-7,17-dione (63). The results of the NMR analysis are set forth in Table Ten.

(Step 3) In a second round bottom flask equipped with a magnetic stirrer was placed 0.155 mmoles of 3β-propionoxy-16α-hydroxy-Δ5-androstene-7,17-dione (63) dissolved in 6 ml of methanol to form a third mixture. To this third mixture was added 1.5 ml of an aqueous solution of 6N sulfuric acid to form a fourth mixture which was maintained at 25° C. for 18 hours. The fourth mixture was then partitioned between ethyl acetate and water and separated by decanting the ethyl acetate phase from the water phase. The ethyl acetate was evaporated to yield an organic product which was purified by chromatography (silica preparative plate eluted three times with 60% ethyl acetate-hexane) to yield 18 mg of an organic compound which was then dissolved in and crystallized from methanol to give 6 mg of substantially pure material having a melting point of 235°–239° C. The organic compound was identified by NMR as 3β,16α-dihydroxy-Δ5-androstene-7,17-dione (6). The results of the NMR analysis are set forth in Table Eleven.

Example IX
(Steroid 7)

Synthesis

Δ5-Androstene-3β-propionoxy-16β-acetoxy-7,17-dione (Step 1) Into a round bottom flask equipped with a magnetic stirrer was placed 1.52 mmoles of 3β-propionoxy-16α-hydroxy-Δ5-androstene-7,17-dione, 3.0 mmoles of triphenylphosphine, 6.0 mmoles of acetic acid in 11 ml of tetrahydrofuran. This first mixture was placed under $N_2$ and cooled to 0° C. in an ice bath. To the first mixture was added 3.0 mmoles of diethyl azodicarboxylate dropwise to form a second mixture. The second mixture was warmed to 25° C. and maintained at this temperature for 18 hr. It was then partitioned between ether-hexane and water. The ether-hexane layer was washed with water, water, saturated $NaHCO_3$ aqueous solution, saturated NaCl aqueous solution, dried over $Na_2SO_4$ and evaporated to give an organic solid which was purified by chromatography on 130 gm silica eluted with ethyl acetate-hexane (20:80 to 50:50) with 25 ml fractions and crystallized from dichloromethane-hexane to yield 0.267 gm of an organic compound. The organic compound was identified by NMR as 3β-propionoxy-16β-acetoxy-Δ5-androstene-7,17-dione containing ~20% of the 16α epimer. The results of the NMR analysis are see forth in Table Twelve.

(Step 2) Conversion to Δ5-androstene-3β,16β-dihydroxy-7,17-dione can be done as described in Example VIII.

Example X
(Steroid 8)

Synthesis

Δ5-Androstene-3β,7α,17β-triol-16-one (Step 1) Into a 100 ml round bottomed flask was placed 3 grams (7.7 mmoles) of 3β,16α-diacetoxy DHEA (prepared in accordance with the procedure set forth in Numazawa, M. and Osawa, Y. *Steroids*, vol. 32, p 519 (1978)) and 3.5 grams $NaHCO_3$ in 50 ml of hexane to form a first mixture. The first mixture was stirred and heated to reflux under a $N_2$ atmosphere. To the first mixture was added 1.6 grams dibromantin (1,3-dibromo-5,5-dimethylhydantoin) to form a second mixture.

(Step 1) The second mixture was stirred, refluxed for 30 minutes, and then cooled to room temperature. The refluxed second mixture was filtered to remove solids and washed with $CH_2Cl_2$. The resultant filtrate was concentrated to near dryness in vacuo using a water bath maintained below 35° C.

(Step 3) The dried filtrate was resolubilized in 21 ml of toluene in a one liter stoppered flask equipped with a magnetic stirrer and placed in an ice bath. Into the resolubilized filtrate was added 2.1 grams anhydrous LiBr in 80 ml ice-cold acetone to form a third mixture. The third mixture was shielded from light and stirred continuously for three hours at 0° C. The resulting mixture containing predominantly 7α-bromo was used immediately in step four.

(Step 4) Into a 500 ml flask equipped with a magnetic stirrer was placed 80 ml dichloromethane, 21 ml glacial acetic acid, and 6.7 grams of silver acetate to form a first suspension. The first suspension was stirred continuously for 20 minutes at room temperature. The stirred first suspension was added under constant agitation into the warmed third mixture to form a second suspension. The second suspension was constantly stirred for 30 minutes at room temperature after which the suspension was filtered through a sintered glass funnel to separate a solid residue. The filtrate was concentrated to yield an oily residue.

(Step 5) To the oily residue was added 300 ml $H_2O$ and sufficient $NaHCO_3$ to achieve a fourth mixture with a neutral pH. The fourth mixture was extracted five times with 150 ml of ethyl acetate, the organic layers combined, washed with brine, dried over $MgSO_4$ and concentrated to dryness.

(Step 6) The crude organic phase was separated by chromatography (silica gel eluted with ethyl acetate:pet ether at 1:3, 1:2 and 1:1) to yield 700 mg (20%) of a first organic fraction and 1.5 grams (48%) of a second organic fraction. After crystallization from diethyl ether the first (mp 170°–172° C.) and second (mp 155°–158° C.) organic fractions were identified by NMR as Δ5-androstene-3β,7α,16α-triacetoxy-17-one and the corresponding Δ5-androstene-3β,16α-diacetoxy-7α-ol-17-one (83) respectively. The results of the NMR analysis of these two compounds are set forth in Tables Thirteen and Fourteen.

(Step 7) Into a flask equipped with a magnetic stirrer was added 400 mg (1 mmole) of the Δ5-Androstene-3β,16α-diacetoxy-7α-hydroxy-17-one (83) and 342 mg of $K_2CO_3$ in 25 ml of methanol at room temperature to form a fifth mixture. The fifth mixture was stirred for two hours. The alkaline solution enolized the 17-keto to form the more stable 17-hydroxy-16-one compound. Δ5-Androstene-3β,7α,17-trihydroxy-16-one (8) was isolated from the fifth mixture by filtering to remove the insoluble salt, evaporating the methanol in vacuo, purifying the organic residue over silica gel and crystallizing the organic compound from methanol-ethyl ether solution. The crystallized organic fraction (180 mg, 56%; mp: >230° C.) was identified by NMR as Δ5-androstene-3β,7α,17-trihydroxy-16-one (8). The results of the NMR analysis are set forth in Table Fifteen.

Example XI
(Steroid 9)

Synthesis

Δ5-Androstene-3β,17β-diol-7,16-dione (Step 1) Into a round bottom flask equipped with a magnetic stirrer was added 1.05 grams (2.80 mmoles) Δ5-androstene-3β-propionoxy-16α-hydroxy-7,17-dione (63), 80 ml methanol and 40 ml of a 5% aqueous $Na_2CO_3$ solution while stirring rapidly to form a first mixture. The first mixture was stirred for 42 hours after which the methanol was evaporated and a combination of 100 ml of water and 2 ml of acetic acid added to form a second mixture. A solid material was filtered from the second mixture, resolubilized in methanol and then crystalized to yield 0.324 gm of an organic compound.

A small sample of the organic compound was again recrystalized from methanol to produce a purified sample having a melting point of 215°–218° C. The first organic compound was identified by NMR as Δ5-androstene-3β,17β-diol-7,16-dione. The results of the NMR analysis are set forth in Table Sixteen.

TABLE ONE

NMR Results
3β-acetoxy-17-hydroxy-Δ5,Δ16-androstadiene-7-one-trimethylsilyl ether (52a)

| Conditions | Peak | Significance |
|---|---|---|
| (δ) $CDCl_3$ | 0.21 | s, O—SiMe$_3$ |
| 270 MHz | 0.87 | s, 18-CH$_3$ |
|  | 1.25 | s, 19-CH$_3$ |
|  | 2.07 | s, CH$_3$COO |
|  | 2.75 | ddd, J=14, 6, 3, Hz 15α-H |
|  | 4.54 | dd, J=3, 1.5Hz 16-H |
|  | 4.73 | tt, J=11, 5Hz 3α-H |
|  | 5.76 | d, J=2Hz 6-H |

TABLE TWO

NMR Results
3β-(trimethylsilyl)acetoxy-17-hydroxy-Δ5,Δ16-androstadiene-7-one trimethylsilyl ether (52b)

| Conditions | Peak | Significance |
|---|---|---|
| (δ) $CDCl_3$ | 0.13 | s, C—SiMe$_3$ |
| 270 MHz | 0.21 | s, O—SiMe$_3$ |
|  | 0.87 | s, 18-CH$_3$ |
|  | 1.25 | s, 19-CH$_3$ |
|  | 1.90 | s, CH$_2$—Si |
|  | 2.75 | ddd, J=14, 6, 3, Hz 15α-H |
|  | 4.54 | dd, J=3, 1.5Hz 16-H |
|  | 4.73 | tt, J=11, 5Hz 3α-H |
|  | 5.76 | d, J=2Hz 6-H |

TABLE THREE

NMR Results
3β-acetoxy-16α-phenylseleno-Δ5-androstene-7,17-dione (53a)

| Conditions | Peak | Significance |
|---|---|---|
| (δ) $CDCl_3$ | 0.92 | s, 18-CH$_3$ |
| 270 MHz | 1.21 | s, 19-CH$_3$ |
|  | 2.07 | s, CH$_3$COO |
|  | 3.00 | ddd, J=14, 5, 0.5 Hz 15α-H |
|  | 4.10 | d, J=7.5Hz $J_{SeH}$=5Hz 16β-H |
|  | 4.73 | tt, J=11, 5Hz 3α-H |
|  | 5.74 | d, J=1.5Hz 6-H |
|  | 7.31 | m, SePh |
|  | 7.68 | m, SePh |

TABLE FOUR

NMR Results
3β-(trimethylsilyl)acetoxy-16α-phenylseleno-
Δ5-androstene-7,17-dione (53b)

| Conditions | Peak | Significance |
|---|---|---|
| (δ) CDCl$_3$ | 0.13 | s, C—SiMe$_3$ |
| 200 MHz | 0.91 | s, 18-CH$_3$ |
| | 1.21 | s, 19-CH$_3$ |
| | 1.91 | s, CH$_2$Si |
| | 3.00 | ddd, J=14 5.5, 0.5Hz 15α-H |
| | 4.10 | d, J=7.5Hz J$_{SeH}$=5Hz 16β-H |
| | 4.73 | tt, J=10.5Hz 3α-H |
| | 5.74 | d, J=1.5Hz 6-H |
| | 7.32 | m, SePh |
| | 7.68 | m, SePh |

TABLE FIVE

NMR Results
3β,16-diacetoxy-Δ5-androstene-
16-phenylseleno-7,17-dione (55)

| Conditions | Peak | Significance |
|---|---|---|
| (δ) CDCl$_3$ | 1.25 | s, 18-CH$_3$ |
| 200 MHz | 1.35 | s, 19-CH$_3$ |
| | 2.05 | s, 3-CH$_3$COO |
| | 2.09 | s, 16-CH$_3$COO |
| | 3.20 | dd, J=14.5, 6Hz 15α-H |
| | 4.73 | tt, J=11, 5.5Hz 3α-H |
| | 5.74 | d, J=1.5Hz 6-H |
| | 7.35 | m, SePh |
| | 7.68 | m, SePh |

TABLE SIX

NMR Results
3β,16-diacetoxy-Δ5,Δ15-androstadiene-
7,17-dione (57)

| Conditions | Peak | Significance |
|---|---|---|
| (δ) CDCl$_3$ | 1.24 | s, 18-CH$_3$ |
| 200 MHz | 1.30 | s, 19-CH$_3$ |
| | 2.07 | s, 3-CH$_3$COO |
| | 2.25 | s, 16-CH$_3$COO |
| | 4.75 | tt, J=11, 5Hz 3α-H |
| | 5.83 | d, J=1.5Hz 6-H |
| | 7.82 | broad s, 15-H |

TABLE SEVEN

NMR Results
3β-acetoxy-Δ5-androstene-7,16,17-trione (5)

| Conditions | Peak | Significance |
|---|---|---|
| (δ) CDCl$_3$ | 1.07 | s, 18-CH$_3$ |
| 270 MHz | 1.30 | s, 19-CH$_3$ |

TABLE SEVEN-continued

NMR Results
3β-acetoxy-Δ5-androstene-7,16,17-trione (5)

| Conditions | Peak | Significance |
|---|---|---|
| | 2.05 | s, 3-CH$_3$COO |
| | 2.44 | dd, J=18.5, 8Hz 15β-H |
| | 2.61 | m, 4-H |
| | 3.43 | dd, J=18.5, 6.5Hz 15α-H |
| | 4.75 | tt, J=11, 5Hz 3α-H |
| | 5.80 | d, J=1.5Hz 6-H |

TABLE EIGHT

NMR Results
3β-propionoxy-Δ5-androstene-7,17-dione (61)

| Conditions | Peak | Significance |
|---|---|---|
| (δ) CDCl$_3$ | 0.91 | s, 18-CH$_3$ |
| 270 MHz | 1.16 | t, J=7.5Hz CH$_3$CH$_2$COO |
| | 1.25 | s, 19-CH$_3$ |
| | 2.15 | dt, J=19, 8.5Hz 16α-H |
| | 2.33 | q, J=7.5Hz CH$_3$CH$_2$COO |
| | 2.83 | dddd, J=15.5, 8.5, 4, 1Hz 15α-H |
| | 4.75 | tt, J=11, 5Hz 3α-H |
| | 5.77 | d, J=2Hz 6-H |

TABLE NINE

NMR Results
3β-propionoxy-17-hydroxy-Δ5, Δ16-
androstadiene-7-one trimethylsilyl ether (62)

| Conditions | Peak | Significance |
|---|---|---|
| (δ) CDCl$_3$ | 0.18 | s, Si—Me$_3$ |
| 270 MHz | 0.85 | s, 18-CH$_3$ |
| | 1.13 | t, J=7.5Hz CH$_3$CH$_2$COO |
| | 1.21 | s, 19-CH$_3$ |
| | 2.14 | ddd, J=14.8, 10.7, 1.5Hz 15β-H |
| | 2.31 | q, J=7.5Hz CH$_3$CH$_2$COO |
| | 2.71 | ddd, J=14.8, 6.4, 2.1Hz 15α-H |
| | 4.52 | dd, J=3.1, 1.5Hz 16-H |
| | 4.72 | tdd, J=11.4, 5.3, 4.4Hz 3α-H |
| | 5.71 | d, J=1.6Hz 6-H |

TABLE TEN

NMR Results
3β-propionoxy-16α-hydroxy-Δ5-androstene-7,17-dione (63)

| Conditions | Peak | Significance |
|---|---|---|
| (δ) CDCl$_3$ | 1.00 | s, 18-CH$_3$ |
| 270 MHz | 1.15 | t, J=7.5Hz |
| | | CH$_3$CH$_2$COO |
| | 1.23 | S, 19-CH$_3$ |
| | 2.33 | q, J=7.5Hz |
| | | CH$_3$CH$_2$COO |
| | 2.75 | ddd, J=13.5, 6.5, 1.5Hz |
| | | 15α-H |
| | 4.42 | d, J=8Hz |
| | | 16β-H |
| | 4.76 | tt, J=10.5, 4.5 Hz |
| | | 3α-H |
| | 5.77 | d, J=1.5Hz |
| | | 6-H |

TABLE ELEVEN

NMR Results
3β,16α-dihydroxy-Δ5-androstene-7,17-dione (6)

| Conditions | Peak | Significance |
|---|---|---|
| (δ) CDCl$_3$ | 1.00 | s, 18-CH$_3$ |
| 270 MHz | 1.23 | s, 19-CH$_3$ |
| | 2.26 | ddd, J=14.5, 10.5, 8.6Hz |
| | | 15β-H |
| | 2.55 | ddd, J=14.1, 5.0, 1.3Hz |
| | | 4α-H |
| | 2.76 | ddd, J=14.6, 6.9 1.4Hz |
| | | 15α-H |
| | 3.69 | broad t, J=11Hz |
| | | 3α-H |
| | 4.41 | d, J=8.5Hz |
| | | 16β-H |
| | 5.75 | d, J=1.7Hz |
| | | 6-H |

TABLE TWELVE

NMR Results
3β-propionoxy-16β-acetoxy-Δ5-androstene-7,17-dione (7)

| Conditions | Peak | Significance |
|---|---|---|
| (δ) CDCL$_3$ | 1.00 | s, 18-CH$_3$ |
| 270 MHz | 1.15 | t, J=7.5Hz |
| | | CH$_3$CH$_2$COO |
| | 1.25 | s, 19-CH$_3$ |
| | 2.12 | s, CH$_3$COO |
| | 2.33 | q, J=7.5Hz |
| | | CH$_3$CH$_2$COO |
| | 3.35 | ddd, J=11, 8.5 4Hz |
| | | 15α-H |
| | 4.74 | tt, J=11, 4Hz |
| | | 3α-H |
| | 5.77 | d, J=1.5Hz |
| | | 6-H |

TABLE THIRTEEN

NMR Results
Δ5-Androstene-3β,16α-diacetoxy-7α-hydroxy-17-one (83)

| Conditions | Peak | Significance |
|---|---|---|
| (δ) CDCl$_3$ | 0.98 | s, CH$_3$ |
| 300 MHz | 1.02 | s, CH$_3$ |
| | 2.02 | s, 2xCO$_2$CH$_3$ |
| | 2.10 | s, CO$_2$CH$_3$ |
| | 4.70 | m, 1H, 3-H |
| | 5.02 | dd, 1H, J=2Hz 7-H |
| | 5.40 | d, 1H, J=4Hz 16-H |
| | 5.61 | d, 1H, J=2Hz 6-H |

TABLE FOURTEEN

NMR Results
Δ5-androstene-3β,16α-diacetoxy-7α-ol-17-one

| Conditions | Peak | Significance |
|---|---|---|
| (δ) CDCl$_3$ | 0.97 | s, CH$_3$ |
| 300 MHz | 1.02 | s, CH$_3$ |
| | 2.04 | s, CO$_2$CH$_3$ |
| | 2.15 | s, CO$_2$CH$_3$ |
| | 3.92 | m, 1H, 7-H |
| | 4.63 | m, 1H, 3-H |
| | 5.44 | d, 1-H, J=5Hz 16-H |
| | 5.64 | d, 1-H, J=4Hz 6-H |

TABLE FIFTEEN

NMR Results
Δ5-androstene-3β,7α,17-trihydroxy-16-one (8)

| Conditions | Peak | Significance |
|---|---|---|
| (δ) DMSO | 0.61 | s, CH$_3$ |
| 300 MHz | 0.92 | s, CH$_3$ |
| | 3.32 | m, 3-H |
| | 3.60 | broad s 1H, 7-H |
| | 3.64 | s, 1H, 16-H |
| | 4.26 | d, 1H, J=2Hz OH, D$_2$O exch. |
| | 4.68 | broad s, 1H OH, D$_2$O exch. |
| | 5.30 | broad s, 1H OH, D$_2$O exch. |
| | 5.42 | d, 1H, J=2Hz 6-H |

TABLE SIXTEEN

NMR Results
3β,17β-dihydroxy-Δ5-androstene-7,16-dione (9)

| Conditions | Peak | Significance |
|---|---|---|
| (δ) CDCl$_3$ | 0.75 | s, 18-CH$_3$ |
| 270 MHz | 1.26 | s, 19-CH$_3$ |
| | 3.15 | ddd, J=19, 7, 1.5Hz |
| | | 15α-H |
| | 3.72 | tt, J=10, 4.5Hz 3α-H |

TABLE SIXTEEN-continued

NMR Results
3β,17β-dihydroxy-Δ5-
androstene-7,16-dione (9)

| Conditions | Peak | Significance |
|---|---|---|
| | 3.78 | broad s<br>17α-H |
| | 5.77 | d, J=1.5Hz<br>6-H |

I claim:

1. A method of abating weight gain comprising the step of administering to a subject prone to weight gain an effective weight gain controlling amount of a steroid selected from the group consisting of
Δ5-Androstene-3β-acetoxy-7,16,17-trione
Δ5-Androstene-3β,16α-dihydroxy-7,17-dione
Δ5-Androstene-3β-propionoxy-16β-acetoxy-7,17-dione
Δ5-Androstene-3β,7α,17β-triol-16-one
Δ5-Androstene-3β,17β-diol-7,16-dione
Δ5-Androstene-3β,16α,17β-triol,7-one
and derivatives thereof wherein one or more of the hydroxyl or keto substituents is a group convertible thereto by hydrolysis.

2. The method of claim 1 wherein the step of administering a steroid to a subject comprises the step of administering a steroid to a mammal.

3. The method of claim 2 wherein the step of administering a steroid to a mammal comprises the step of administering a steroid to a human.

4. The method of claim 3 wherein the step of administering an effective weight gain controlling amount of a steroid comprises the step of administering about 0.1 to 2 grams of the steroid per 100 kg body weight per day.

5. The method of claim 3 wherein the step of administering an effective weight gain controlling amount of a steroid comprises the step of administering a therapeutic dose of the steroid at least once a week.

6. The treatment method of claim 3 wherein the step of administering an effective weight gain controlling amount of a steroid comprises the step of administering a therapeutic dose of the steroid at least once a day.

7. The treatment method of claim 3 wherein the step of administering an effective weight gain controlling amount of a steroid comprises the step of injecting the human with a therapeutic dose of the steroid.

8. The treatment method of claim 3 wherein the step of administering an effective weight gain controlling amount of a steroid comprises the step of inducing the human to ingest a therapeutic dose of the steroid.

9. A method of promoting weight loss comprising the step of administering to a subject in need of such treatment an effective weight reduction promoting amount of a steroid selected from the group consisting of
Δ5-Androstene-3β-acetoxy-7,16,17-trione
Δ5-Androstene-3β,16α-dihydroxy-7,17-dione
Δ5-Androstene-3β-propionoxy-16β-acetoxy-7,17-dione
Δ5-Androstene-3β,7α,17β-triol-16-one
Δ5-Androstene-3β,17β-diol-7,16-dione
Δ5-Androstene-3β,16α,17β-triol,7-one
and derivatives thereof wherein one or more of the hydroxyl or keto substituents is a group convertible thereto by hydrolysis.

10. The method of claim 9 wherein the step of administering a steroid to a subject comprises the step of administering a steroid to an overweight human.

11. A method of treating obesity comprising the step of administering to an obese subject a therapeutic amount of a steroid selected from the group consisting of
Δ5-Androstene-3β-acetoxy-7,16,17-trione
Δ5-Androstene-3β,16α-dihydroxy-7,17-dione
Δ5-Androstene-3β-propionoxy-16β-acetoxy-7,17-dione
Δ5-Androstene-3β,7α,17β-triol-16-one
Δ5-Androstene-3β,17β-diol-7,16-dione
Δ5-Androstene-3β,16α,17β-triol,7-one
and derivatives thereof wherein one or more of the hydroxyl or keto substituents is a group convertible thereto by hydrolysis.

12. The method of claim 11 wherein the step of administering a steroid to a subject comprises the step of administering the steroid to a human.

* * * * *

UNITED STATES PATENT AND TRADEMARK OFFICE
CERTIFICATE OF CORRECTION

PATENT NO. : 5,506,223

DATED : 09 April 1996

INVENTOR(S) : Henry A. Lardy, Ieva L. Reich and Yong Wei

It is certified that error appears in the above-identified patent and that said Letters Patent is hereby corrected as shown below:

Col. 7, Line 40, delete "$\beta$", insert --$\alpha$--

Col. 10, Line 14, delete "tile", insert --the--

Col. 13, Line 43, delete "mole", insert --mmole--

Col. 13, Line 47, delete "moles", insert --mmoles--

Col. 15, Line 5, delete "0,500", insert --0.500--

Col. 21, Table 12, Line 51, delete "$CDCL_3$", insert --$CDCl_3$--

Col. 24, Line 39, delete "the", insert --a--

Signed and Sealed this

Twenty-seventh Day of August, 1996

BRUCE LEHMAN

Attest:

Attesting Officer

Commissioner of Patents and Trademarks